United States Patent [19]

Lejeune

[11] Patent Number: 4,683,345
[45] Date of Patent: Jul. 28, 1987

[54] PREPARATION AND USE OF SUBSTITUTED BISPHENOLS

[75] Inventor: Guy Lejeune, Neuilly-Sur-Seine, France

[73] Assignee: Colette Nouvel, France

[21] Appl. No.: 852,409

[22] Filed: Apr. 16, 1986

[30] Foreign Application Priority Data

Apr. 16, 1985 [FR] France .................................. 85 05681

[51] Int. Cl.$^4$ .............................................. C07C 39/16
[52] U.S. Cl. .................................... 568/726; 568/727; 568/728
[58] Field of Search ......................... 568/726, 727, 728

[56] References Cited

U.S. PATENT DOCUMENTS

| | | | |
|---|---|---|---|
| 1,977,627 | 10/1934 | Greenhalgh | 568/727 |
| 3,426,081 | 2/1969 | Shore et al. | 568/726 |
| 3,674,879 | 7/1972 | Tiefenthal et al. | 568/726 |
| 4,535,191 | 8/1985 | Mark et al. | 568/726 |

FOREIGN PATENT DOCUMENTS 1208325 10/1970 United Kingdom ............... 568/726

*Primary Examiner*—Werren B. Lone
*Attorney, Agent, or Firm*—Ostrolenk, Faber, Gerb & Soffen

[57] ABSTRACT

Process of preparation of a bisphenol by the condensation of a phenol carrying a halogen substituent and alkyl groups with an aldehyde in a solvent for the phenol, in the presence of sulphuric acid; the proportion of acid with respect to the phenol is such that after the condensation and absorption by the acid of the water eliminated, the acid contains less than 50% of water by weight.

17 Claims, No Drawings

PREPARATION AND USE OF SUBSTITUTED BISPHENOLS

The invention relates to an improved process for the production of bisphenols formed by the interconnection of two molecules of a phenol substituted with a divalent group —CRH—. It also comprises uses of such compounds and more particularly those where the phenolic rings each carry as substituents a halogen and two alkyl groups.

In pharmacology, methylene-2,2'-bis-(4-chlorothymol) is known which under the commercial name BICLOTYMOL has been a remarkable medicament for 20 years. It is particularly active against infections by Gram+ bacteria, particularly staphylococci, streptococci, and pneumococci (U.S. Pat. No. 3,716,646 or GB-B-1129826). Such bisphenols are prepared easily by the action of an aldehyde, in particular formaldehyde, paraformaldehyde or dioxane, on two moles of the corresponding substituted phenol, which gives by condensation:

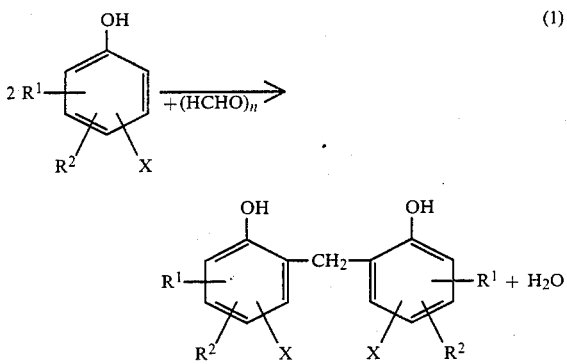

where $R^1$ and $R^2$ are alkyl groups and X is a halogen.

It is known however that if a very pure bisphenol is to be prepared, it is necessary to submit the product obtained to expensive and troublesome purification operations. It is in fact accompanied by a coloured substance, apparently a polymer, which is insoluble in solvents for bisphenol, which carries the risk of causing difficulties in various uses, particularly in therapeutics and cosmetics. This disadvantage is particularly apparent when the 6-position ortho to the OH group is occupied by an alkyl group and particularly by a branched alkyl group. This is the reason why it is not possible to obtain products according to the formula (1) suitably by the known method which consists in reacting an aldehyde with 2 moles of the substituted phenol in an excess of sulphuric or phosphoric acid, as described in U.S. Pat. Nos. 3,426,081 and 3,723,541 or French No. 2091408 and GB No. 893162. Since this prior art relates to the preparation of methylene-2,2'-bistrichlorophenols which are stable compounds soluble in alkaline bases, these impurities can be eliminated by dissolution of the bisphenol in an alkaline base solution, as indicated for example in FR No. 2091048, page 3 lines 14 to 37, in U.S. Pat. No. 2,435,593 or U.S. Pat. No. 3,426,081, col. 3 lines 18 to 30. However, the bisphenols prepared according to the present invention are only "cryptophenols" which are practically insoluble in bases. They thus cannot be purified by the known method even though they are very impure and coloured when they are prepared in an excess of acid.

Moreover, they cannot be prepared by the process described in DE-2418975, using small catalytic quantities of phosphoric acid at a temperature of 110° to 180° C., because the conversion rates are poor and the product is very impure.

In the face of these difficulties, the present invention provides an unexpected result by using a solvent for the substituted phenol containing a certain specific proportion of concentrated sulphuric acid and by carrying out the condensation with the aldehyde at a moderate temperature adjusted to be between 40° to 65° C. In these special conditions, in a surprising manner substituted bisphenols according to formula (1) are obtained practically without polymers and with a low colouration which disappears on the recrystallisation. The product so obtained can have a higher purity than 99.5%.

The proportion of concentrated sulphuric acid according to the invention per mole of phenol is very different from that used in the prior art: it must be chosen much lower than in the U.S., French and British patents cited above where it constitutes the reaction medium in the ratio of 200 to 600 g per mole of phenol, but is much higher than the solely catalytic quantity according to the cited German specification where the maximum is 16 g per mole of phenol. Thus the principle of the invention is different; the quantity of acid is just sufficient to bind all the water formed by condensation of the phenol with the aldehyde without the concentration of the acid falling below a value for which the vapour pressure of the water would no longer be negligible.

The proportion of acid according to the invention must be such that after the reaction during which the acid has absorbed the water of condensation, the acid so diluted still contains more than 50% by weight of $H_2SO_4$. Preferably, it is such that the acid still contains 70 to 95% by weight of $H_2SO_4$ after the reaction.

This requires the addition of 21 to 171 g of $H_2SO_4$ per mole of phenol utilized, this acid preferably being taken in the form of the 80 to 100% acids.

The reaction can take place between 40° and 65° C. and preferably from 60° to 65° C. but without exceeding this latter limit.

It is advantageous to employ a certain excess of the aldehyde with respect to the stoichiometric quantity. The excess preferred is about 2 to 20%, that is 1.02 to 1.20 mole of aldehyde per 2 moles of substituted phenol employed.

The solvent or solvents in which the reaction (1) is carried out can be selected from all solvents for the substituted phenol which is condensed with the aldehyde. However, hydrocarbons boiling below 100° C. or slightly above this temperature are preferred. Thus, $C_5$ to $C_8$ alkanes are particularly preferred, as well as chlorinated $C_1$ to $C_3$ hydrocarbons, particularly pentanes, hexanes, heptanes, octanes, methyl chloride or methylene chloride, dichloromethane, chloroform, dichloroethane, trichloroethane, dichloroethylene, trichloroethylene, etc., and mixtures thereof.

Solvents capable of forming azeotropic mixtures with water and boiling below 100° C. are for example benzene, toluene, chloroethylene, chloropropylene, n or isopropanol, the butanols etc.

It has been found that the bisphenols when they are prepared in accordance with the invention have a considerably increased solubility in their organic solvents. Thus for example 1% solutions of methylene-2,2'-bis(4-chloro-3-methyl-6-isopropyl)phenol in a mixture of 40 parts by weight of water with 60 parts of alcohol can easily be prepared.

It is known that the halogen substituents of phenol having a methylene bridge increase the microbicidal and fungicidal powder of phenolic derivatives. As a representative example, methylene-2,2'bis(4-chloro-3-methyl-6-isopropyl)phenol known in pharmacy under the name BICLOTYMOL presents a marked anti-bacterial action, particularly against Gram positive organisms, particularly staphilococcus London and 133, streptococcus, pneumococcus etc. which is more pronounced than that of hexachlorophene. Also, its low toxicity, the $DL_{50}$ exceeding 11.8 g/kg, markedly differentiates it from other chlorinated derivatives of diphenylmethane, in particular hexachlorophene. This considerable advantage allows its use without danger by internal or external administration routes.

On the other hand, it has been shown that BICLOTYMOL also exhibits an antiinflammatory and antalgic activity, evidenced by the LEVY method on the one hand and the KOSTER method on the other, in comparison with acetyl salicylic acid and oxyphenbutazone. BICLOTYMOL has significant anti-inflammatory and antalgic acitivities, proportional to the doses used, but lower than those which are necessary in the case of the products in question.

Owing to the very low toxicity indicated below for compounds of the formula 1 when $R^1$ and $R^2$ are $C_1$ to $C_3$ and X is chlorine, these find interesting uses in areas related to human and animal feeding. In particular, these compounds are well suited to the external anti-infection treatment of mamella.

Cow udders are particularly subject to infection because of the presence of milk, which is an excellent nutritive medium for bacteria. The method which consists in the prolonged use of penicillin leads to penicillin-resistant bacteria; the penicillin residues or the products of decomposition are found in the milk. Despite precautions taken throughout a period of years, contaminated milk becomes absorbed by humans who in their turn become carriers of bacteria resistant to penicillin. By contrast, none of this is produced with the compounds prepared according to the invention, although mastitis is effectively combatted. The non-toxicity of these compounds means that there is no risk of contamination of the milk. Other veterinary compositions in the form of liquid emulsions or ointments in association with one or more bactericidal agents and a solvent suitable from the physiological standpoint can be used for other animal diseases.

As a composition for local application, use can be made of certain forms already described for oral administration by adding to them liquid or solid soaps, in the presence of surfactants which do not inhibit the bactericidal action of the active principles; anti-sebborrheic shampoo can also be included in this category, together with toothpastes.

Compounds for the throat, the nose and for the disinfection of wounds comprising non-irritant solvents are particularly appreciated and efficaceous. The various active principles described above can also be formulated in all ways concerned in dermopharmacy, particularly cosmetic and deodorant creams. They are particularly effective against acne.

While the present invention applies to the various bisphenols defined above under (1), it gives notable results with the compounds:

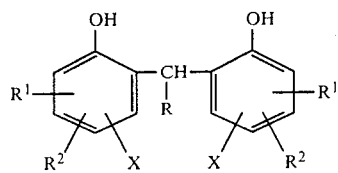

where R is H or a $C_1$ to $C_4$ alkyl group, $R^1$ is a $C_2$ or $C_5$ alkyl group and particularly an iso-isomer, $R^2$ being H, $CH_3$ or $C_2H_5$ and X being chlorine or bromine.

Particularly acitve compounds, which can be obtained according to the invention in good yields and in an excellent state of purity, are those in which R is H, $R^1$ is isopropyl, isobutyl or isoamyl situated alpha or beta with respect to —OH, $R^2$ is a methyl or ethyl alpha or gamma to $R^1$ while X is a Cl para to the OH.

Non-limitative examples which follow illustrate the invention.

EXAMPLE 1

Preparation of methylene-2,2'-bis(4-chloro-3-methyl-6-isopropyl)-phenol

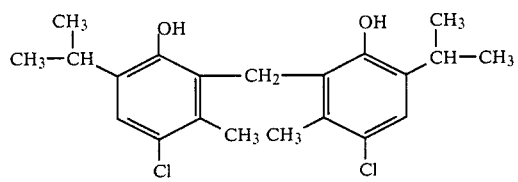

185 g of 4-chloro thymol (1 mole) dissolved in 150 ml of heptane as well as 17.5 g of paraformaldhyde (0.583 mole HCHO) are introduced into a 500 ml reactor. Then 15 ml of 98% sulphuric acid is slowly poured in with agitation while cooling so that the temperature of the mixture does not exceed 65° C. Agitation is continued for 2 hours while maintaining the temperature between 60° and 65° C. The reaction being terminated, the mixture is allowed to cool to ambient temperature and the sulphuric acid layer is decanted from the organic phase. The crystals formed are dried and washed with distilled water to eliminate $SO_4$ ions.

After drying, they are recrystallised from a mixture of 90% hexane and 10% acetone.

The bisphenol so obtained is a white solid melting at 126° to 130° C. It dissolves without difficulty or colouration in the solvent mixture indicated above, contrary to the corresponding product prepared in the usual manner without the addition of $H_2SO_4$. The yield in comparison with the phenol is 68%.

In this Example, the quantity of water formed by the reaction is 9 g; as 27 g of 98% sulphuric acid (15 ml) has been added this, after absorbtion of 9 g $H_2O$, titrates as $(98 \times 27):(27+9)=73.5\%$ $H_2SO_4$.

EXAMPLE 2

The operations of Example 1 are repeated, with the difference that the initial chlorothymol is taken into solution in 1,2-dichloroethane in place of heptane. The results are practically the same, which shows that operation can equally well take place in solution in an alkane as in a halogeno-alkane.

EXAMPLE 3

Preparation of methylene-2,2'-bis(4-chloro-5-methyl-6-isopropyl)phenol (compound II), that is the isomer of product I of Examples 1 and 2 in which the —CH$_3$ is found in the 5 position instead of the 3 position with respect to the —OH.

Operation takes place exactly as in Example 1 with 185 g of 4-chloro-5-methyl-6-isopropyl phenol in place of the 4-chlorothymol. The resultant bisphenol obtained is soluble without residue in solvents, in particular in the hexane-acetone mixture. Re-crystallised, this compound II has a melting point of 131° to 133° C. Yield in comparison with the phenol is 70%.

EXAMPLE 4

The preparation of Example 3 is repeated, this time with 1,2-dichloroethane as the solvent in place of the heptane for the initial substituted phenol. The compound II obtained is even more pure than in Example 3.

EXAMPLE 5

Preparation of methylene-2,2'-bis(4-chloro-3-methyl-5-isopropyl)phenol (compound III), that is the isomer of compound I of Examples 1 and 2 in which the isopropyl group is in the 5 position instead of the 6 position with respect to the —OH.

The mode of operation is the same as in Example 1, the 4-chloro-thymol used being replaced by 185 g (1 mole) of (4-chloro-3-methyl-5-isopropyl)phenol in solution in heptane.

The compound III thus obtained in soluble without difficulty or residue in its solvents. It melts at 173° to 175° C. after recrystallisation. Yield 75%.

EXAMPLE 6

In the mode of operation as in Example 5, the heptane is replaced by 1,2-dichloro-ethane. The results are practically the same as in Example 5.

EXAMPLE 7

The operations of Example 1 are repeated, but the volume of 98% sulphuric acid added is only 2 ml, namely 3.67 g of H$_2$SO$_4$ in place of 27 g. The product obtained in a yield of 39% is dark pink coloured, melting at 120° C. in place of 126° to 130° C. as in Example 1. It is not usable for pharmaceutical purposes. This result shows the disadvantage of small catalytic proportions of the acid.

EXAMPLE 8

The operations of Example 1 are repeated with 120 ml of 98% sulphuric acid, namely 220 g of H$_2$SO$_4$ as against 15 ml (=27 g) of Example 1. The product obtained is a dark mass containing black particles. To decolourise it, it is necessary to add active carbon to the solution in 90 parts of hexane with 10 parts of acetone prepared for the purposes of recrystallisation. The crystals obtained are yellow and it is necessary to carry out two recrystallisations in the presence of active carbon to obtain a final colourless product. Yield over the chlorothymol . . . 35%.

It can be seen that the preparation becomes difficult if the limit of 171 g H$_2$SO$_4$ per mole of phenol is exceeded.

EXAMPLE 9

Fungicidal Composition for Agricultural Use 1 kg of compound II (according to Examples 3 or 4) is dissolved in 100 liters of 70% ethanol (30% by weight of water) containing 0.15 kg of nonyl phenyl polyethylene glycol ether, known in commerce under the name "TERGITOL NP-44" as a surfactant. At the time of use, this composition is diluted 1/10 with water and is sprayed on to plants affected by cryptogamic diseases.

EXAMPLE 10

Liquid composition for washing bovine or ovine udders in cases of mastitis. By weight 2% of compound I (formula I—Example 1), 30% of propylene glycol, 20% polyethylene glycol, 48% water.

EXAMPLE 11

Formulations of compositions for the topical treatment of acne. Quantities by weight:

| (a) | compound I | 1.5 | (b) | compound I | 2.0 |
|---|---|---|---|---|---|
| | erythromycin | 4.0 | | retinoic acid | 0.3 |
| | zinc orotate | 2.0 | | zinc orotate | 1.0 |
| | ethanol | 60.0 | | ethanol | 33.0 |
| | water to make | 100 | | water to make | 100 |
| (c) | Skin Gel: | | | | |
| | Compound I | | 1.0 | | |
| | Benzoyl peroxide | | 7.0 | | |
| | Excipient gel to make | | 100 | | |

EXAMPLE 12

Scab-forming and tissue regeneration composition particularly for treatment after burns or sunstroke. By weight: compound I . . . 2; zinc orotate . . . 3.5; 95° ethanol . . . 60; water to make 100.

EXAMPLE 13

Antiseborrheic and anti-inflammatory shampoos or lotions. By weight:

| (a) | compound I | 1.5 | (b) | hydro-alcoholic gel | 1 |
|---|---|---|---|---|---|
| | zinc orotate | 3.5 | | compound I | |
| | 60° ethanol | qs | | Carbopal 934 | 1 |
| | | for 100 | | ethanol | 40 |
| | | | | water | 58 |
| | | | | pH adjusted to 5 | |
| | | | | with caustic soda | |
| (c) | compound I | 3 | (d) | compound I | 2 |
| | dihydroxy-methyl lauramide | 5 | | Na alkyl-ether-sulphate | 1 |
| | pure water | 92 | | zinc orotate | 1 |
| | pH adjusted to 5 with caustic soda | | | pure water | 96 |

EXAMPLE 14

Scab-forming aerosol.

| Compound I | 1 |
|---|---|
| Catalase Fraction of horse liver | $2 \times 10^7$ IU |
| Saccharose to make 100 | |

EXAMPLE 15

Antihelmintic compositions.

| (a) | compound 1 | 2 | (b) | compound 1 | 0.50 |
| --- | --- | --- | --- | --- | --- |
| | piperazine hydrate | 12 | | levamisole | 0.15 |
| | saccharose | 86 | | hydrochloride | |
| | | | | dose for 1 tablet | |

I claim:

1. In the process of preparation of a bisphenol by condensing a phenol, carrying a halogen substituent and alkyl groups, with an aldehyde in a solvent for the phenol in the presence of sulfuric acid, the improvement which comprises the proportion of acid with respect to the phenol being 21 to 171 g $H_2SO_4$ per mole of phenol such that, after the condensation and absorption by the acid of the water eliminated, the acid contains less than 50% of water by weight, and the reaction takes place at a temperature in the range from 40° to 65° C.

2. A process according to claim 1, in which the proportion of acid is such that, after the condensation, the acid contains 70% to 95% $H_2SO_4$ by weight.

3. Process according to claim 1, in which the acid before the condensation has a concentration of 80%–100%.

4. A process according to claim 1, in which the temperature is in the range from 60° to 65° C.

5. A process according to claim 1, in which the solvent is a $C_5$ to $C_8$ alkane.

6. A process according to claim 2, in which the phenol has the formula:

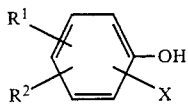

where $R^1$ is a $C_2$ to $C_5$ alkyl group, $R^2$ is H or a $CH_3$ or $C_2H_5$ group and X is chlorine or bromine.

7. A process according to claim 6, in which $R^1$ is an isopropyl group, $R^2$ is a methyl group located in the alpha or gamma position relative to the $R^1$ group and X is a Cl atom located in the para position relative to the OH group.

8. A process according to claim 1, in which the phenol is 4-chlorothymol, 4-chloro-5-methyl-6-isopropyl-phenol or 4-chloro-3-methyl-5-isopropyl-phenol and the quantity of aldehyde is 1.02 to 1.2 moles per 2 moles of phenol.

9. A method of preparing a bisphenol which comprises condensing a phenol of the formula:

wherein $R^1$ is a $C_2$ to $C_5$ alkyl group, $R^2$ is hydrogen, methyl or ethyl and X is chlorine or bromine, with an aldehyde RCHO, R being hydrogen or $C_1$ to $C_4$ alkyl, in a hydrocarbon or chlorohydrocarbon solvent for said phenol in the presence of 21 to 171 g of $H_2SO_4$ per mole of phenol in the form of an aqueous acid having at least 80% $H_2SO_4$ by weight, at a temperature of 40° to 65° C., and recovering the bisphenol thus formed.

10. A method according to claim 9 wherein the amount of aldehyde is 1.02 to 1.2 moles per 2 moles of phenol.

11. A method according to claim 10 wherein said temperature is 60° to 65° C.

12. A method according to claim 9, wherein the aldehyde and $H_2SO_4$ are added to the phenol dissolved in the solvent with cooling such that the temperature does not exceed 65° C.

13. A method according to claim 9, wherein the phenol is 4-chloro-thymol.

14. A method according to claim 9, in which the phenol is 4-chloro-5-methyl-6-isopropyl-phenol.

15. A method according to claim 9, in which the phenol is 4-chloro-3-methyl-5-isopropyl-phenol.

16. A method according to claim 9, wherein the hydrocarbon solvent is pentane, hexane, heptane or octane.

17. A method according to claim 9, wherein the chlorohydrocarbon solvent is methyl chloride, methylene chloride, chloroform, dichloroethane or trichloroethylene.

* * * * *